United States Patent [19]

Unland et al.

[11] 4,115,424

[45] Sep. 19, 1978

[54] ZEOLITE CATALYST

[75] Inventors: Mark L. Unland; George E. Barker, both of St. Louis, Mo.

[73] Assignee: Monsanto Company, St. Louis, Mo.

[21] Appl. No.: 753,041

[22] Filed: Dec. 22, 1976

[51] Int. Cl.² .................. B01J 21/02; B01J 27/34; B01J 29/06
[52] U.S. Cl. .................. 252/432; 252/437; 252/455 Z; 260/669 R
[58] Field of Search .................. 252/432, 437, 455 Z; 260/669 R, 671 C

[56] References Cited

U.S. PATENT DOCUMENTS

| | | |
|---|---|---|
| 3,598,879 | 8/1971 | Kmecak et al. ............... 252/432 X |
| 3,674,425 | 7/1972 | Robson .......................... 252/455 Z |
| 3,780,125 | 12/1973 | Takacs ........................... 252/455 Z |
| 3,962,364 | 6/1976 | Young ............................ 252/437 X |
| 4,009,217 | 2/1977 | Uitti ............................... 260/669 R |

Primary Examiner—Carl F. Dees
Attorney, Agent, or Firm—Joseph D. Kennedy; John D. Upham

[57] ABSTRACT

An improved alkylation catalyst is provided exemplified by a type X or Y zeolite with cesium, rubidium or potassium cations, and with a boron or phosphorous component added. The catalyst is useful in producing styrene from toluene and methanol.

12 Claims, No Drawings

ZEOLITE CATALYST

This invention relates to particular modified zeolite catalysts and their uses in alkylation of toluene to styrene and ethylbenzene.

BACKGROUND OF THE INVENTION

Various alumina-silicate catalysts have been known for various alkylations of aromatic compounds, such as the X- or Y- type zeolites described in U.S. Pat. No. 3,251,897. The alkylation of toluene with methanol in the presence of a cation exchanged zeolite has been described by Yashima et al in the Journal of Catalysis, Vol 26, 303–312 (1972), with styrene and ethylbenzene included in products produced.

SUMMARY OF THE INVENTION

It has now been found that certain additives result in improvement of particular zeolite catalysts for the production of styrene and ethylbenzene in alkylation reactions. The improved zeolite catalysts have boron or phosphorous incorporated therein, with the zeolite being a crystalline aluminosilicate of the faujasite structure with $SiO_2/Al_2O_3$ mole ratio in the range of about 2 to about 8, and with some portion of the alkali metal present being potassium, rubidium, cesium, or mixtures thereof. The zeolites utilized are exemplified by X- and Y- type zeolites, and cesium is the preferred cation, with a major amount of the sodium or other cation generally present being replaced by the cesium. The improved catalysts can be utilized in an improved process for producing styrene and ethylbenzene by alkylation of toluene with alkylating agents such as methanol, with improved selectivity to such products and/or higher ratio of styrene to ethylbenzene in the product. Procedures are provided for incorporating the boron or phosphorous components.

DETAILED DESCRIPTION OF THE INVENTION

Styrene is a commodity chemical sold and utilized in extremely large volume for producing polystyrene and other products. Hence any process for producing styrene is of great interest if it offers a potential advantage in cost or in availability of reactant materials. Toluene and methanol are potentially attractive source materials for production of styrene, and the present invention provides an improved process for producing styrene from such materials. Zeolites have previously been employed for alkylation of toluene to styrene, but zeolites are capable of catalyzing a variety of reactions, and therefore generally produce a variety of materials along with the desired alkylation product. In the present invention a catalyst is provided which gives improved selectivity to the desired styrene and ethylbenzene products, often with a high ratio of styrene in such products. The catalysts also in general have good activity, in many cases giving higher conversions than previously known zeolite catalysts for such reactions.

In the production of styrene and ethylbenzene, the present catalysts can be employed under conditions generally used in alkylation reactions, such as those used in methylation of toluene with other zeolite catalysts, with the selection of particular conditions being influenced by such considerations as activity and temperature stability of the particular catalyst, desired conversion and attainable product selectivity. Temperatures appropriate for alkylations can be used, for example about 350° C. to about 500° C. or so, but preferred temperatures are about 400° C. to 475° C. Higher temperatures can be used, but tend to degrade reactants, and are not necessary as high conversions can be attained in the stated ranges. The reactants can be brought into contact with the catalyst in usual manner, generally as a stream of reactants conducted over or through a bed of catalyst. The contact time can be varied over a wide range, but will generally be selected to obtain an acceptable conversion per pass at the reaction temperature. For example, ranges of gas hourly space velocities from 50 to 5,000 $hr^{-1}$ or more are operable, and good conversions can often be obtained even at reasonably high space velocities such as 500 to 1,500 $hr^{-1}$ or so. The reaction in general will occur as long as quantities of both methanol and toluene are present, in ranges, for example, of 0.5 to 20 or more moles toluene per mole methanol. However, since only one methanol molecule is needed, and to minimize side reactions, the toluene is generally used in excess, often for example, in the range of 2 to 10 or 20 or more moles toluene per mole methanol.

Methylations of toluene can produce some methanol decomposition products, and over some catalysts are capable of producing various xylenes or other alkylated aromatics, as well as some polymer, aromatization and coke materials, along with the styrene and ethylbenzene sought in the process of the present invention. The present invention provides a means of directing the process toward production of styrene and ethylbenzene, and to some extent particularly toward styrene. It is obvious that there is economic advantage in directing the process to desired product at the expense of waste or less desired product. The use of the present improved catalysts increases the selectivity to styrene and ethylbenzene, i.e., it increases the amount of these products obtained per unit of methanol which has reacted. Also, or in some cases alternatively, it increases the amount of styrene in the desired products, i.e., the ratio of styrene to styrene plus ethylbenzene. Both styrene and ethylbenzene are useful products and sought in the present invention. However, the usual use for ethylbenzene is to prepare styrene by dehydrogenation, and therefore styrene is the more valuable product and there is some advantage in directing the process toward styrene at the expense of ethylbenzene.

In the methylation process of the present invention, improved zeolite catalysts containing phosphorus and boron components are utilized. Those with a boron component are preferred, exhibiting marked improvement in selectivity to styrene and ethylbenzene, as well as improvement in the ratio of styrene in such products. The phosphorus component tends to have a stronger effect upon the ratio of styrene than upon selectivity, but nevertheless provides an advantage.

In methylation reactions employing the present catalyst, it is not necessary to employ any diluents as the reactants can simply be conducted over the catalyst. A closed system is utilized, thereby avoiding possible adverse effects of air, moisture, etc. but it is not necessary to rigidly exclude such materials by removing all traces from the system. Over a period of time the catalyst is subject to loss of activity from carbon deposition etc. and can be regenerated by heating in air to remove the carbon.

Zeolites are known for the alkylation of toluene to styrene and ethylbenzene, and in general zeolites suitable for such reaction can be modified as taught herein to provide the improved catalysts of the present invention. For example, the X- or Y- type zeolites described in the aforesaid U.S. Pat. No. 3,251,897, or the zeolites described in the aforesaid Journal of Catalysts publication, including those for which original sources are cited therein. As taught herein, the modification will include a cation exchange to provide potassium, rubidium, or cesium ions, if not already present, and the incorporation of boron or phosphorus into the zeolite. In general suitable zeolites will be of the faujasite structure with an $SiO_2/Al_2O_3$ mole ratio in the range of about 2 to about 8. A number of zeolites having higher silica to alumina ratios, such as 12 or much higher, have recently been advanced for various aromatization and alkylation reactions, but in general do not appear suitable for use in the present invention. With regard to structural classification, those zeolites with a double 6-ring or faujasite structure are generally suitable for use herein. Such zeolites characteristically have pore diameters in excess of 6 angstroms, which is appropriate for admission of methanol and toluene, and to allow exit of styrene and ethylbenzene. The X- and Y- type zeolites have been found very suitable for modification and use herein, with the X-type being particularly preferred. Type X has a typical oxide formula $Na_2O.Al_2O_3.2.5SiO_2.6H_2O$ with $SiO_2/Al_2O_3$ in the range of 2.0–3.0. Type Y has a typical oxide formula $Na_2O.Al_2O_3.4.8SiO_2.8.9-H_2O$ with $SiO_2/Al_2O_3$ range from 3.0–6.0. Type L zeolites and natural faujasite materials are examples of other zeolites having appropriate pore size and structure for use herein. In general, zeolites having suitable properties can be utilized, whether obtainable as natural materials or prepared synthetically, and can be obtained from commercial sources or prepared by appropriate laboratory crystallization procedures.

The zeolites utilized herein are modified to have potassium, rubidium or cesium ions present, individually or together. Usual ion exchange procedures can be employed to replace the sodium, hydrogen or other ions of the zeolite with the desired cations. If equivalent zeolites could be prepared directly with the desired cations, the zeolites could be utilized herein, but present practice is to prepare the zeolites by ion exchange procedures. In theory, 81% of sodium on type X and 71% on type Y is exchangeable, and it will ordinarily be desirable to exchange 50% or more for potassium, rubidium or cesium. Smaller portions, for example 20 or 30% or more, will have some effect and provide improved catalysts as taught herein, but the improvement is generally enhanced with increasing percentage change, up to 60% or so. Above about 60%, improvement is not apparent, and the usual exchange procedures do not readily produce exchanges above 65% or so or closely approach the theoretical. For the catalysts herein, cesium is the preferred cation for the zeolite. The boron and phosphorus additives have a desired effect on the rubidium and potassium exchanged materials, which in some aspects is very marked, but the cesium zeolite even without additional additive, is generally better, and with the additive boron or phosphorus gives superior selectivity to styrene and ethylbenzene or a better ratio of styrene, and often better activity as well. At times it may be convenient or desirable to employ a mixture of cations, such as a mixture of rubidium and cesium, and, of course the common preparations generally result in a mixture of a minor amount of sodium with one of the other cations.

The present improved catalysts include a boron or phosphorus element or compound. The additional component serves as a promoter to cause some reactions to be favored at the expense of others. A small amount of the boron or phosphorus is sufficient, but the effective amounts are not narrowly critical. While extremely small amounts will have some effect, an amount sufficient to approach optimum effectiveness will preferably be used. Excess over the optimum can be used, but large excesses will not give any additional benefit, and may tend to cause unnecessary loss of catalyst activity because of diluent or other effect. Generally the amounts employed will not be in excess of 5% by weight of the boron or phosphorus, on an elemental basis, and usually in the range of about 0.1% to about 2% by weight. The amounts have reference to the amount in the catalyst, rather than the amounts used in the preparation, which often are much larger, depending upon method of preparation.

The particular form of the boron or phosphorus component has not definitely been ascertained, but it has been found effective and apparently boron or phosphorus components retained in the catalyst, if not in proper form, are converted into effective form either in the catalyst preparation or under use conditions. Presumably boron and phosphorus are in some oxide form, and there is some evidence that the boron is actually bonded to the zeolite. Thus preparation methods are used which result in retention of the boron or phosphorus in the zeolite, and various compounds and procedures have been found suitable for this purpose. The boron and phosphorus components can be added to the zeolite during cation exchange procedures, or in subsequent treatments. After the boron or phosphorus component has been incorporated, there appears to be some potential loss by leaching or exchange, so it is generally preferred to avoid excessive washing or similar procedures subsequent to incorporation of the boron or phosphorus. Also it will be undesirable to subject the catalyst to treatments known to cause loss of cations by exchange with hydrogen or other ions. Moreover, the selection of solvents for exchange or impregnation procedures has an influence on retention of the components in the catalyst. Solutions or slurries of boron or phosporus compounds in such solvents as acetone, methanol, etc. can be used. Alternatively, the boron or phosphorus can be incorporated by physical admixture of the oxides or other liquid or solid compounds into the zeolite, generally in powdered or other particulate form. Various forms of the compounds can be used, e.g. sodium or potassium tetraborate, $B_2O_3$, boric acid, tripentyl borate, trimethoxy borate, phosphoric acid and its esters, e.g. trimethoxyphosphate, $K_3PO_4$, etc. Other forms of boron or phosphorus can readily be selected which can conveniently be employed to result in incorporation of boron or phosphorus into the catalyst. In general any methods of contacting the catalyst with boron or phosphorus in a form resulting in retention in the catalyst are suitable. While the catalyst will generally be prepared in advance of use, it is considered feasible to introduce boron or phosphorus into the catalyst along with alkylation process reactants, as by adding a volatile boron or phosphorus compound to the reactants and contacting the catalyst zeolite material therewith, or by introducing such boron or phosphorus compound with inert diluent prior to introduction of the reactants. As illustrated herein, the boron or phosphorus component can conveniently be incorporated by inclusion in an ion exchange solution, or by subsequently utilizing a solution of such component as a slurrying medium for catalyst particles or as an impregnating medium to be absorbed in the catalyst. The media for incorporating the boron and phosphorus do not necessarily have to completely dissolve the boron or phosphorus material, and in fact may often contain suspended solids.

The catalyst is generally dried following impregnation or other liquid treatment procedures, as by heating at about 100° C. for a sufficient time, but such procedure can be omitted. The catalyst can be activated by calcining, i.e., heating to elevated temperatures, usually as high as the contemplated reaction-use temperature, and often higher. Activation temperatures in the general range of 400° to 650° C. or so can be used, ordinarily in a stream of air or inert gas. It is preferred to activate in a flowing stream to mitigate possible adverse effects of water being removed, but this precaution is not essential to the preparation of the present improved catalyst. The heating will cause fusion and/or decomposition of many boron or phosphorus compounds, thereby possibly resulting in closer association with the zeolite.

The present catalyst is adaptable to use in the various physical forms in which catalysts are commonly used, as particulate material in a contact bed, or a coating material on monolithic structures, generally being used in a form to provide high surface area. The catalyst can if desired be composited with various catalyst binder or support materials which do not adversely affect the catalyst or the reactions in which the catalyst is to be employed.

The present catalysts are well suited for use in the methylation of toluene to styrene. However, the catalysts are also contemplated as having utility in various condensation type reactions. Acidic zeolite catalysts, which have various known uses, can often be converted to basic catalysts by ion exchange with such ions as cesium. Such basic catalysts tend to convert methanol, apparently through an intermediate, to carbon monoxide, rather than to dimethylether. Borate modification of the catalyst makes it slightly less basic, but it retains selectivity to carbon monoxide in methanol reactions. Thus the catalyst may be useful in various reactions of methanol involving production of carbon monoxide as an intermediate. The catalyst may also find use in other reactions of toluene involving activation such that reaction occurs at the methyl group rather than on the ring.

The following examples are illustrative of the invention.

EXAMPLE 1

A zeolite catalyst with cesium cation and boron additive was prepared as follows. One liter of an aqueous solution was prepared containing 75 grams CsOH and 50 grams $H_3BO_3$. Twenty grams of a type X zeolite (Linde SK20) was ion exchanged with a 300 ml portion of the solution with stirring at about 100° C. for 2 hours. The exchange procedure was repeated for 3 hours with another 300 ml. portion of the solution. The procedure was then repeated overnight using the remaining 400 ml. solution. The solid zeolite was then dried at 100° C. in air for 4 hours. The resulting solid powder was pressed under pressure into 1 inch disks, which were then crushed and screened into 8 × 30 mesh particles. The catalyst can then be activated by heating to about reaction temperature, or approximately 450° C., in inert gas, such as a flowing nitrogen stream, or in air. The thus prepared catalyst is suitable for methylation of toluene, with very good selectivity to styrene and ethylbenzene. In procedures utilizing 14 different samples of such catalyst, in reacting methanol with toluene at 410° C. to about 60% conversion of the methanol, the average selectivity to styrene plus ethylbenzene was 50%, with the ratio of styrene to styrene plus ethylbenzene being 38%. This compares to a selectivity of 39.7% and ratio of 21% for a control catalyst having cesium in a type X zeolite, prepared by the same procedure but without the boron component. Considered on a basis of 80% conversion, the selectivity for the boron-containing catalyst is 48.4%, compared to 35.2% for the control catalyst.

EXAMPLE 2

Catalyst samples were prepared by an ion exchange procedure as described in Example 1, but without boric acid in the exchange solution. Boric acid was then added to the catalyst by slurrying the cesium zeolite obtained from 20 grams of zeolite X, with a solution of a measured amount of boric acid in 100 grams of methanol. The slurry was stirred for 5 to 10 minutes or so, and the catalyst solids were separated and treated as in Example 1. The catalyst was then used to methylate toluene be reaction of toluene and methanol supplied in about 5:1 mole ratio and contacting the catalyst at a bed temperature of 410° C. The results are reported in Table 1.

Table 1
Toluene Methylation
Cesium zeolite with $H_3BO_3$ Added (methanol)

| Catalyst | $H_3BO_3$ in solution (grams) | Conversion | Selectivity (S + EB) | Ratio | $S_{80}$ | Coke |
|---|---|---|---|---|---|---|
| A | 0 | 46 | 46 | 30 | 36.5 | 5.1 |
| B | 1 | 44 | 54.4 | 35 | 46.8 | 9.4 |
| C | 2 | 51 | 55.0 | 41 | 52.0 | 13.0 |
| D | 3 | 62 | 49.0 | 67 | 47.3 | 18.7 |
| E | 4 | 64 | 49.4 | 66 | 48.6 | 20.9 |

In the above table, and for other data reported herein, conversion is based on methanol, and is the percentage of methanol in the reactant stream which has been converted to other compounds. Selectivity (S + EB) is the percentage of methanol converted which is found as styrene and ethylbenzene. $S_{80}$ is the selectivity at 80 conversion of the methanol. Ratio is styrene compared to styrene plus ethylbenzene, on a mole percentage basis. "Coke" is a relative number, indicating the tendency of the catalyst to form carbon, with higher values indicating more carbon.

The data indicates that the presence of boron results in improvement in selectivity to styrene and ethylbenzene as well as an increase in the ratio of styrene in that product. Conversions are also increased, indicating good activity even at a temperature of only 410° C. Such converions are obtainable at gaseous hourly space velocities of 950 $hr^{-1}$, and faster space velocity will generally lower conversions, while slower space velocities raise conversions. The improved selectivity and therefore higher yield of styrene was obtained despite the higher carbon formation indicated by the coke index.

The results in the methylation reactions herein are largely reported on the basis of methanol, as the yields based on toluene are generally very high, while the methanol is the reactant with a tendency to undergo side or decomposition reactions and with regard to which improvement over previously known procedures is sought.

EXAMPLE 3

Catalysts were prepared as in Example 2, but utilizing acetone as the solvent in the slurrying operation, rather than methanol. The catalyst was then used to methylate toluene with methanol at 950 hr$^{-1}$ space velocity as in Example 2, but at a temperature of 450° C., with results as reported in Table 2.

Table 2

Toluene Methylation
Cesium zeolite with H$_3$BO$_3$ Added (Acetone)

| Catalyst | H$_3$BO$_3$ in solution (grams) | Conversion | Selectivity (S + EB) | Ratio | S$_{80}$ | Coke |
|---|---|---|---|---|---|---|
| F | 0 | 99 | 29.4 | 8 | 41.6 | 7.4 |
| G | 0.5 | 98 | 44.9 | 27 | 46.9 | 13.8 |
| H | 1.0 | 97 | 46.8 | 43 | 48.6 | 12.5 |
| I | 2.0 | 92 | 43.7 | 76 | 46.9 | 7.2 |

The presence of boron again improves selectivity to styrene and ethylbenzene, and the ratio of styrene in the product. Also the coke formation was lower than with some other catalysts. Referring particularly to catalyst I, the conversion, selectivity and ratio were all high, resulting in a very good styrene monomer yield, 33% per pass. Acetone has advantage as a solvent for addition of boron or other components subsequent to the zeolite preparation, as it has less tendency than more polar solvents to cause ion exchange or similar reactions which result in loss of cations.

EXAMPLE 4

Cesium exchanged zeolite X was prepared as in Example 1, but without boron additive. Twenty gram portions of the zeolite were used. The resulting cesium zeolite was then impregnated with a boron compound by treating the zeolite with approximately an equal weight of methanol, containing one gram of a boron compound. The zeolite was then vacuum dried and activated for catalytic use. Results for reaction of methanol and toluene at 410° C. and under previously described conditions are reported in Table 3.

Table 3

Toluene Methylation
Cesium Zeolite with Boron Compound Impregnated

| Catalyst | Boron Compound | Conversion | Selectivity (S + EB) | Ratio | S$_{80}$ | Coke |
|---|---|---|---|---|---|---|
| J | None | 67 | 34.9 | 17 | 33.3 | 6.7 |
| K | H$_3$BO$_3$ | 68 | 44.6 | 55 | 44.8 | 16.5 |
| L | B$_2$O$_3$ | 60 | 44.0 | 80 | 45.9 | 16.1 |
| M | Na$_2$B$_4$O$_7$ | 77 | 43.3 | 27 | 43.3 | 10.6 |

The various forms of added boron resulted in improved selectivity.

EXAMPLE 5

Catalysts were prepared from type X (Linde SK 20) and type Y (Linde SK 40) zeolites, by exchange with cesium hydroxide in water. Additional catalysts were prepared under the same conditions, but with phosphoric or boric acid added in the exchange solution, to bring it to a pH of 10. The catalysts were employed in the reaction of methanol and toluene at 950 hr$^{-1}$ gaseous hourly space velocity and 450° C., with results reported in Table 4.

Table 4

Methylation of Toluene
Cesium Zeolites with Phosphorous or Boron

| Catalyst | Zeolite | Additive | Conversion | Selectivity (S + EB) | Ratio | S$_{80}$ | Coke |
|---|---|---|---|---|---|---|---|
| N | X | H$_3$PO$_4$ | 99 | 35.2 | 42 | 41.4 | 14.7 |
| O | Y | H$_3$PO$_4$ | 85 | 26.5 | 70 | — | — |
| P | X | H$_3$BO$_3$ | 100 | 44.3 | 34 | 46.8 | 19.9 |
| Q | Y | H$_3$BO$_3$ | 64 | 37.4 | 71 | 37.4 | 4.1 |
| R | X | None | 100 | 25.0 | 1 | 34.4 | 6.0 |
| S | Y | None | 93 | 16.5 | 13 | 17.7 | 3.3 |

Active catalysts are formed from both X and Y type zeolites, and both phosphorus and boron have a beneficial effect on selectivity of the catalysts.

EXAMPLE 6

A type X zeolite was treated in an ion exchange procedure to produce a cesium exchanged zeolite, and 21.5 grams of the particulate material was physically mixed with 1 gram of boric acid. The material was pressed into disks which were then broken into particulate material and activated as catalyst by heating in the reactor. At a temperature of 410° C., the material was effective for methylation of toluene, giving selectivity of 49.1% to styrene plus ethylbenzene with a 42% ratio of styrene, conversion of 69% and a coke index of 10.8.

EXAMPLE 7

Portions of a cesium zeolite catalyst were physically admixed with measured amounts of boric acid, to incorporate a specified amount of boric acid into 21-22 grams or so of zeolite, and the catalysts were activated and utilized for methylation of toluene with methanol in a mole ratio of 5.25 to 1, 950 hr$^{-1}$ gaseous hourly space velocity, and temperature of 410° C. Results are reported in Table 5.

Table 5

Methylation of Toluene
Cesium Zeolite - Boric Acid Mixture

| Weight Boric Acid (grams) | Conversion | Selectivity (S + EB) | Ratio | S$_{80}$ | Coke |
|---|---|---|---|---|---|
| 1 | 53 | 52.4 | 35 | 50.6 | 8.9 |
| 2 | 37 | 53.5 | 44 | 46.8 | 5.5 |
| 5 | 16 | 43.1 | 70 | 40 | 1.8 |

EXAMPLE 8

Procedures are known in which catalysts have been prepared from type X zeolite by ion exchange to have rubidium or potassium ions. Procedures as described in Example 1 can be employed. Similar exchanges were run in which phosphoric acid had been added to the alkali hydroxide exchange solution (to pH 10). The catalysts were activated and employed in a reaction of toluene and methanol at 5.25/1 mole ratio at 410° C., and 950 hr$^{-1}$ space velocity. Results, along with those for reference catalysts, are reported in Table 6.

Table 6

Toluene Methylation
Catalyst with H$_3$PO$_4$

| Catalyst Cation | Additive | Conversion | Selectivity (S + EB) | Ratio | S$_{80}$ | Coke |
|---|---|---|---|---|---|---|
| Cs | None | 61 | 44.6 | 27 | 39.5 | 8.3 |
| Cs | H$_3$PO$_4$ | 62 | 44.4 | 66 | 41.4 | 14.7 |
| Rb | None | 61 | 28.2 | 24 | 26.7 | 7.9 |
| Rb | H$_3$PO$_4$ | 43 | 42.6 | 44 | 32.7 | 6.6 |
| K | None | 57 | 21.4 | 37 | 21.0 | 7.6 |
| K | H$_3$PO$_4$ | 45 | 21.1 | 60 | 21.6 | 6.0 |

The results were fairly good with all of the catalysts, including those with potassium and rubidium as cation, and the phosphoric acid improved the ratio of styrene in the product.

Rubidium and potassium zeolite catalysts were prepared as in Example 8, from X type zeolite, but with boric acid (to pH 10) in the alkali metal hydroxide exchange solution. The catalysts were employed in the reaction of toluene and methanol (5.25:1 mole ratio in feed) at 410° C. and 950 hr$^{-1}$. Results, along with those of reference catalysts, are reported in Table 7.

Table 7

| Catalyst Cation | Additive | Methylation of Toluene Catalyst with H$_3$BO$_3$ | | | | |
|---|---|---|---|---|---|---|
| | | Conversion | Selectivity (S + EB) | Ratio | S$_{80}$ | Coke |
| Cs | None | 61 | 44.6 | 27 | 39.5 | 8.3 |
| Cs | H$_3$BO$_3$ | 58 | 51.9 | 29 | 49.8 | 9.2 |
| Rb | None | 61 | 28.2 | 24 | 26.7 | 7.9 |
| Rb | H$_3$BO$_3$ | 40 | 40.2 | 31 | 36.5 | 6.0 |
| K | None | 57 | 21.4 | 37 | 21.0 | 7.6 |
| K | H$_3$BO$_3$ | 44 | 22.5 | 62 | 24.6 | 7.3 |

The boric acid resulted in improved catalysts, note the improvement in S$_{80}$ in each case over the reference catalyst.

In the conversion of toluene to styrene and ethylbenzene over the catalysts of the present invention, reactants other than methanol can be used. Such reactants are for convenience termed "methylating" agents herein, although styrene does not actually differ from toluene by a methyl group. Methanol and formaldehyde, or various forms or sources of formaldehyde can be used, e.g. trioxane, methylal, paraformaldehyde, or commercial formaldehyde solutions such as Formcel formaldehyde solution (55% formaldehyde, 10% water and balance methanol).

EXAMPLE 9

A boron-containing catalyst was prepared in accordance with the procedure of Example 1, but employing a type X zeolite prepared in the laboratory and very similar to SK 20 zeolite used in Example 1. The catalyst was employed under the usual conditions in the reaction of methanol and toluene (5.25 moles/1 mole) with results as follows Table 8

| Temperature | Conversion | Selectivity (S + EB) | Ratio |
|---|---|---|---|
| 450° C | 98 | 48.3 | 10 |
| 430° C | 85 | 54.2 | 18 |
| 410° C | 60 | 58.3 | 24 |

The effluent sample for the 450° C. readings was taken after the feed was on stream for ten minutes, the 430° C. sample after an additional 17.5 minutes, and the 410° C. sample after an additional 17.5 minutes.

The boron-containing catalyst described above was utilized in a reaction of trioxane with toluene. A feed of 30 moles toluene/1 mole s-trioxane (10/1 mole toluene/CH$_2$O) was employed at the usual space velocity and at 400° C. An effluent sample was taken after 17 minutes, and an additional sample after 37 minutes, with results as follows:

Table 9

| Time | Conversion | Selectivity (S + EB) | Ratio | Coke |
|---|---|---|---|---|
| 17 min. | 100 | 41.9 | 75 | 15 |
| 37 min. | 100 | 36.5 | 77 | 18 |

The results indicate the boron-containing catalyst was successfully used for reacting trioxane and toluene to form styrene and ethylbenzene. The trioxane utilized was s-trioxane, m.p. 58°–60° C., mol. wt. 90.08.

After the reaction with trioxane, the coke was burned off the catalyst for 38 minutes (16 millimoles coke) and the catalyst was then utilized for reacting toluene and methanol (5.25/1 mole ratio) at 400° C., with a sample after 5 minutes showing 49% conversion, 53.5% selectivity, a ratio of 43%, and coke 9.8.

In the production of styrene and ethylbenzene according to the present invention formaldehyde, or forms or derivatives of formaldehyde producing formaldehyde in situ can be employed and are contemplated in the use of formaldehyde described herein. Also it will be recognized that various industrial sources of methanol or formaldehyde are available, as for example methanol produced in a methanol reformer from carbon monoxide and hydrogen obtained in a cracking process.

What is claimed is:

1. A catalyst comprising a crystalline aluminosilicate zeolite of the faugasite structure with SiO$_2$/Al$_2$O$_3$ mole ratio in the range of about 2 to about 8 and including potassium, rubidium or cesium cations or combinations thereof, and containing boron or phosphorus or combinations thereof.

2. The catalyst of claim 1 containing boron.

3. The catalyst of claim 1 in which the zeolite includes cesium cation.

4. The catalyst of claim 3 containing boron.

5. The catalyst of claim 1 in which boron has been introduced by addition of boric acid.

6. The catalyst of claim 1 in which boron has been introduced by addition of an oxide of boron.

7. The catalyst of claim 1 in which potassium, rubidium or cesium cations have been introduced into a type X or Y zeolite by ion exchange procedures to have at least 50% of the potential alkali metal content as such cations.

8. The catalyst of claim 7 in which cesium is at least 60% of the potential alkali metal.

9. The catalyst of claim 8 in which the zeolite is type X.

10. The catalyst of claim 8 containing boron.

11. The catalyst of claim 10 in which boron is present in an amount of 0.1% to 2% by weight of the catalyst.

12. The catalyst of claim 1 in which boron or phosphorus are present in amounts no greater than 5% by weight of the catalyst.

* * * * *